(12) United States Patent
Cotteret

(10) Patent No.: US 6,238,439 B1
(45) Date of Patent: *May 29, 2001

(54) METHOD FOR DYEING KERATINOUS FIBERS WITH INDOLE COMPOUNDS, COMPOSITIONS AND DEVICES FOR IMPLEMENTATION

(75) Inventor: Jean Cotteret, Verneuil-sur-Seine (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/405,993

(22) Filed: Mar. 17, 1995

Related U.S. Application Data

(63) Continuation of application No. 08/049,584, filed on Apr. 21, 1993, now abandoned, which is a continuation-in-part of application No. 07/718,778, filed on Jun. 21, 1991, now abandoned.

(30) Foreign Application Priority Data

Jun. 21, 1990 (FR) .................................................. 90 07752

(51) Int. Cl.$^7$ ...................................................... A61K 7/13
(52) U.S. Cl. ........................................ 8/409; 8/407; 8/423
(58) Field of Search ............................... 8/405, 406, 408, 8/414, 416, 423, 407, 409

(56) References Cited

U.S. PATENT DOCUMENTS

| | | | |
|---|---|---|---|
| 2,934,396 | 4/1960 | Charle et al. | 8/11 |
| 4,013,404 | 3/1977 | Parent et al. | 8/11 |
| 4,804,385 | 2/1989 | Grollier et al. | 8/423 |
| 4,808,190 | 2/1989 | Grollier et al. | 8/423 |
| 4,885,006 | 12/1989 | Grollier et al. | 8/423 |
| 4,888,027 | 12/1989 | Grollier et al. | 8/423 |
| 5,034,015 | 7/1991 | Junino et al. | 8/423 |
| 5,131,911 | 7/1992 | Lang et al. | 8/405 |
| 5,346,509 * | 9/1994 | Schultz et al. | 8/423 |

FOREIGN PATENT DOCUMENTS

| | | |
|---|---|---|
| 0271186 | 6/1988 | (EP) . |
| 1166172 | 11/1958 | (FR) . |
| 2636237 | 3/1990 | (FR) . |
| 2640504 | 6/1990 | (FR) . |
| 2649887 | 1/1991 | (FR) . |
| 2187456 | 9/1987 | (GB) . |
| 2207443 | 2/1989 | (GB) . |

* cited by examiner

*Primary Examiner*—Caroline D. Liott
(74) *Attorney, Agent, or Firm*—Pillsbury Winthrop LLP

(57) ABSTRACT

Method for dyeing keratinous fibers, in particular, human keratinous fiber such as hair, without the use of iodide ions wherein a tinctorial composition containing, in a cosmetically acceptable medium having a pH of less than or equal to 7, at least one indole derivative corresponding to the formula

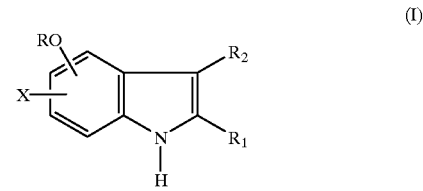

(I)

in which:

$R_1$ denotes hydrogen, alkyl or COOH;

$R_2$ denotes hydrogen or alkyl;

R denotes hydrogen, $Si(CH_3)_3$, or COalkyl; and

X denotes hydrogen, OH, or $OSi(CH_3)_3$; it being possible for X in the 4- or 5-position also to denote the O-alkyl group, on condition that when X is in the 5-position with the meanings mentioned above and OR denotes OH in the 4- or 6-position, only one of the group $R_1$ and $R_2$ then differs from hydrogen;

that when X denotes hydrogen, OR must be in the 7-position and $R_2$ must denote hydrogen; and that when R denotes hydrogen and X denotes OH, OR and X are then in the 5- and the 6-position and $R_1$ denotes COOH, to the fibers in a first step and, after a dwell time followed by rinsing and rubbing dry, applying an alkaline oxidizing solution.

16 Claims, No Drawings

METHOD FOR DYEING KERATINOUS FIBERS WITH INDOLE COMPOUNDS, COMPOSITIONS AND DEVICES FOR IMPLEMENTATION

This is a continuation of application Ser. No. 08/049,584, filed Apr. 21, 1993 now abandoned, which is a continuation-in-part of application Ser. No. 07/718,778 filed Jun. 21, 1991, now abandoned.

BACKGROUND OF THE INVENTION

FIELD OF THE INVENTION

The present invention relates to a method for dyeing keratinous fibers using indole compounds, to the compositions themselves, and to devices for implementation thereof.

The compounds of the indole family, in particular, 5,6-dihydroxyindole and its derivatives, are well known for their use in the dyeing of keratinous fibers and, in particular, of human hair.

The Applicant has discovered that it was possible, with certain indole compounds defined below, to obtain varied shades with glints or natural shades from light to deep blond and warm shades, such as coppery or deep auburn shades, using these indole compounds in a neutral or acid medium. The application of this composition being followed by the application of an alkaline oxidizing composition.

The Applicant has also discovered that by using these specific indole compounds in the method defined above, it was possible to obtain dyes which had good resistance to light and to chemical treatments, such as permanent waving.

The colorings obtained by virtue of the use of these specific indole compounds, within the framework of the method according to the invention, also have the advantage of being uniform, even after several super-positions. They also cover well.

The invention therefore relates to a new dyeing method using certain specific indole derivatives in a cosmetically acceptable medium, at a neutral or acid pH, the application of these derivatives under the indicated pH conditions being followed by the application of an alkaline oxidizing solution.

The invention also relates to the compositions used within the framework of this method.

Further subjects of the invention will become apparent on reading the description and the examples which follow.

The method according to the invention is essentially characterized in that a tinctorial composition containing, in an aqueous cosmetically acceptable medium having a pH of less than or equal to 7, at least one indole derivative corresponding to the formula:

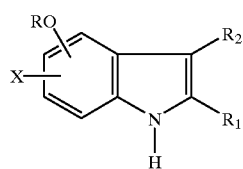

(I)

in which:
$R_1$ denotes hydrogen, alkyl or COOH;
$R_2$ denotes hydrogen or alkyl;
R denotes hydrogen a $Si(CH_3)_3$, or COalkyl group; and
X denotes hydrogen, OH, or $OSi(CH_3)_3$; it being possible for X in the 4- or 5-position also to denote O-alkyl, on condition that when X is in the 5-position and OR denotes OH in the 4- or 6-position, only one of the groups $R_1$ and $R_2$ then differs from hydrogen;

that when X represents hydrogen, OR is in the 7-position and $R_2$ is hydrogen;

that when R denotes hydrogen and X denotes OH, OR and X are, respectively, in the 5- and the 6-position and $R_1$ denotes COOH, and the corresponding acid salts, is applied in a first step and in that, after a dwell time followed by rinsing and rubbing dry, an alkaline oxidizing solution is applied in a second step, this application being followed by rinsing and shampooing.

It should be noted that the present process does not involve the use of iodide ions. Such ions are not included within the initial composition of the first step, nor are they mixed with this composition. The iodide ions also are not included in the alkaline oxidizing solution of the second step.

The Applicant has found that this method enabled varied shades with glints or natural shades from light to deep blond and of copper and deep auburn to be obtained which were uniform after several superpositions and covered the hair well.

In the formula (I), alkyl preferably denotes a radical having 1 to 4 carbon atoms.

The following may be mentioned among the compounds of formula (I) which can be used in this method according to the invention: 7-hydroxy-2,3-dimethyl-4-methoxyindole, 7-hydroxyindole, 5-acetoxy-6-hydroxyindole, 6-hydroxy-2-methyl-5-methoxyindole, 2-carboxy-5,6-dihydroxyindole, 5,6-di(trimethylsilyloxy)indole and 2-methyl-4-hydroxy-5-ethoxyindole.

The compounds particularly preferred are 7-hydroxy-2,3-dimethyl-4-methoxyindole, 7-hydroxyindole, 5-acetoxy-6-hydroxyindole and 2-methyl-4-hydroxy-5-ethoxyindole.

According to a preferred embodiment, these compounds may be used as a mixture with other compounds such as 5,6-dihydroxyindole, 2-methyl-5,6-dihydroxyindole or 6-hydroxyindole and its corresponding acid addition salt.

The indole compound of formula (I) used according to the invention is preferably present in the composition applied in the first step in proportions of between 0.02 and 5% and, in particular, from 0.05 to 3% by weight relative to the total weight of the composition.

The aqueous medium appropriate for dyeing consists of water and preferably a water-solvent(s) mixture, the solvent (s) being chosen from organic solvents such as ethyl alcohol, propyl or isopropyl alcohol, tert-butyl alcohol, ethylene glycol, ethylene glycol monomethyl, monoethyl or monobutyl ethers, propylene glycol, propylene glycol and dipropylene glycol monomethyl ethers and methyl lactate.

The preferred solvents are ethyl alcohol and ethylene glycol monobutyl ether.

The solvent(s) is(are) present in the water/solvent(s) medium in concentrations of between 0.5 and 75% by weight relative to the total weight of the composition and, in particular, between 2 and 50% and preferably between 2 and 20% by weight.

This medium may also contain surface-active agents, which are preferably nonionic, and thickeners well known in the prior art in the field of hair dyeing, such as guar gum, xanthan gum and cellulose polymers, in proportions of between 0 and 3%.

The pH may be adjusted using alkalinizing or acidifying agents customarily used in hair cosmetics.

The composition may also contain adjuvants customarily used in cosmetics, such as perfumes or preservatives.

With a view to varying the shade of the colors obtained with the indole derivatives of formula (I), it is possible to add to the tinctorial composition direct dyes and/or precursors of oxidation dyes and/or couplers and/or rapid oxidation dyes which are well known in the field of hair dyeing, such as, for example, in the publication "HARRY'S COSMETICOLOGY" 7th Edition, edited by J. B. WILKINSON and R. J. MOORE, pages 521 to 545.

The oxidizing composition preferably consists of an aqueous solution of oxidizing agent which is mixed at the time of use with an alkaline aqueous solution which may contain solvents and surface-active agents of the type defined above.

The oxidizing agent is preferably chosen from hydrogen peroxide, urea peroxide and persalts, such as alkali metal or ammonium percarbonates and perborates.

The alkaline agents are chosen from ammonia, alkanolamines such as 2-amino-2-methylpropan-1-ol, monoethanolamine, monomethylethanolamine or dimethylethanolamine.

The aqueous oxidizing agent solution may contain solvents of the type defined above, surface-active agents and also auto-emulsifiable waxes or polyoxyethylenated alcohols to thicken the solutions.

The proportion of oxidizing agent in the composition applied in the second step is between 1 and 15% by weight relative to the total weight of the oxidizing composition, and preferably between 1 and 8% by weight.

The proportion of oxidizing agent in the alkaline oxidizing composition which is applied to the hair is between 1 and 10% by weight relative to the total weight of the composition, and preferably between 1 and 5%.

The pH of the oxidizing composition is between 8.5 and 12.

The invention also relates to a two-component agent for dyeing hair.

The first component (A) consists of a composition containing, in a cosmetically acceptable medium, a compound of formula (I) as defined above and at a pH of less than or equal to 7; the second component (B) consists of an alkaline aqueous solution of an oxidizing agent as defined above.

This dye agent may be packaged in a multi-compartment device or dyeing kit containing, in separate compartments, the components (A) and (B).

Again, it must be noted that iodide ions are not included in component (A) nor are they mixed therewith. Component (B) also does not contain iodide ions.

The following examples are intended to illustrate the invention without, however, having a limiting character.

EXAMPLES 1 TO 5

Hair is dyed by applying 60 g of the coloring composition below.

The composition is allowed to act for 10 minutes, the hair is rinsed with a large amount of water and rubbed dry, and 75 g of the oxidizing composition are then applied, which composition is left on the hair for 10 minutes for Examples 1 and 5 and for 20 minutes for Examples 2, 3 and 4.

After rinsing and shampooing, the coloring indicated at the bottom of the table is obtained.

| in g | 1 | 2 | 3 | 4 | 5 |
|---|---|---|---|---|---|
| Coloring composition | | | | | |
| 7-hydroxy-2,3-dimethyl-4-methoxy-indole | | | | | 0.5 |
| 7-hydroxyindole | 1 | | | 0.05 | |
| 5-acetoxy-6-hydroxyindole | | 0.7 | | | |
| 2-methyl-4-hydroxy-5-ethoxyindole | | | 1 | | |
| 2-methyl-5,6-dihydroxyindole, HBr | | | | 1.5 | |
| 5,6-dihydroxyindole | 0.2 | | | | |
| Ethyl alcohol | 10 | | 10 | 10 | 10 |
| Hydroxyethyl-cellulose sold by HERCULES under the name NATROSOL 250 HHR | 1 | | 1 | 1 | 1 |
| Glycoside alkyl ether sold as a formulation containing 60% AS under the name TRITON CG 110 by SEPPIC | 5 (AS) | | 5 (AS) | 5 (AS) | 5 (AS) |
| Sodium lauryl ether sulphate containing 28% AS | | 4.2 (AS) | | | |
| Ethylene glycol monobutyl ether | | 10 | | | |
| Triethanolamine | | 5 | | | |
| qs pH | | | | | |
| Spontaneous pH | 6.6 | | 6.5 | 6.8 | 6.5 |
| Water qs | 100 | 100 | 100 | 100 | 100 |
| Oxidizing composition | ⅓ A + ⅔ B | ⅓ A + ⅔ B | ⅔ A + ⅓ B | ⅓ A + ⅔ B | ⅓ A + ⅔ B |
| A) Oxyethylenated nonylphenol containing 4 moles of ethylene oxide | 26 | 26 | 26 | 26 | 26 |
| Oxyethylenated nonylphenol containing 9 moles of ethylene oxide | 24 | 24 | 24 | 24 | 24 |
| Ethylene glycol monobutyl ether | 13 | 13 | 13 | 13 | 13 |
| Propylene glycol | 8 | 8 | 8 | 8 | 8 |
| 20% aqueous ammonia solution | 19 | 19 | 19 | 19 | 19 |
| Monoethanolamine | | | | 8 | |
| Oleic acid diethanolamide | 3.5 | 3.5 | 3.5 | 3.5 | 3.5 |
| Perfumes, preservatives, sequestering agent | qs | qs | qs | qs | qs |
| Water qs | 100 | 100 | 100 | 100 | 100 |
| B) 20 volume hydrogen peroxide | | | | | |
| Shades obtained: | ashy light chestnut | golden ashy light blond | deep violet-purple blue | golden coppery deep blond | light auburn |

EXAMPLES 6 TO 9

Hair is dyed by applying 60 g of the coloring composition below.

The composition is allowed to act for 10 minutes, the hair is rinsed with a large amount of water and rubbed dry and 75 g of the oxidizing composition are then applied, which composition is left on the hair for 20 minutes for Examples 6 to 9.

After rinsing and shampooing, the coloring indicated at the bottom of the table is obtained.

|  | 6 | 7 | 8 | 9 |
|---|---|---|---|---|
| Coloring composition |  |  |  |  |
| 7-hydroxyindole |  |  |  | 0.133 |
| 5,6-di(trimethylisilyloxy)indole |  |  | 1 |  |
| 2-methyl-5-methoxy-6-hydroxyindole | 0.5 |  |  |  |
| 2-carboxy-5,6-dihydroxyindole |  | 0.5 |  |  |
| 5,6-dihydroxyindole |  | 0.5 |  |  |
| 6-hydroxyindole |  |  |  | 0.133 |
| p-phenylenediamine |  |  |  | 1.08 |
| p-aminophenol |  |  |  | 0.436 |
| Ethyl alcohol | 10 | 10 | 10 | 10 |
| Hydroxyethylcellulose sold by HERCULES under the name NATROSOL 250 HHR | 1 | 1 | 1 | 1 |
| Glycoside alkyl ether sold as a formulation containing 60% AS under the name TRITON CG 100 by SEPPIC | 5 (AS) | 5 (AS) | 5 (AS) | 5 (AS) |
| Citric acid qs pH |  |  |  | 6.7 |
| Triethanolamine qs pH |  | 6.8 |  |  |
| Spontaneous pH | 6.6 |  | 6.5 |  |
| Water qs | 100 | 100 | 100 | 100 |
| in g |  |  |  |  |
| Oxidizing composition | ⅓ A + ⅔ B | ⅓ A + ⅔ B | ⅔ A + ⅓ B | ⅓ A + ⅔ B |
| A) Oxyethylenated nonylphenol containing 4 moles of ethylene oxide | 26 | 26 | 26 | 26 |
| Oxyethylenated nonylphenol containing 9 moles of ethylene oxide | 24 | 24 | 24 | 24 |
| Ethylene glycol monobutyl ether | 13 | 13 | 13 | 13 |
| Propylene glycol | 8 | 8 | 8 | 8 |
| 20% aqueous ammonia solution | 19 | 19 | 19 | 19 |
| Oleic acid diethanolamide | 3.5 | 3.5 | 3.5 | 3.5 |
| Perfumes, preservatives, sequestering agent | qs | qs | qs | qs |
| Water qs | 100 | 100 | 100 | 100 |
| B) 20 volume hydrogen peroxide |  |  |  |  |
| Shades obtained: | golden natural light blond | golden ashy light chestnut | Ashy very light blond | Golden Coppery blond |

What is claimed is:

1. A process for dyeing keratinous fibers, without iodide ions, consisting essentially of initially applying to said fibers a tinctorial composition consisting essentially of, in a cosmetically acceptable medium having a pH less than or equal to 7, one or more indole derivatives of formula (I)

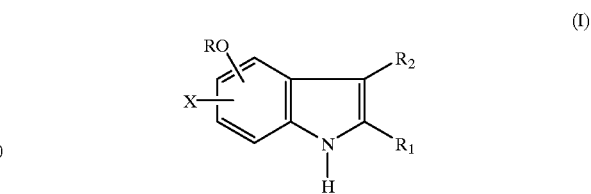

(I)

wherein
  $R_1$ represents hydrogen or alkyl,
  $R_2$ represents hydrogen or alkyl,
  R represents hydrogen, $Si(CH_3)_3$ or CO alkyl, and
  X represents hydrogen, OH or $OSi(CH_3)_3$, or X, when in the 4- or 5-position, also represents O-alkyl on the condition
  that when X is in the 5-position and X is as defined above and OR represents OH in the 4- or 6-position, only one of $R_1$ and $R_2$ is other than hydrogen; and
  that when X represents hydrogen, OR is in the 7-position and $R_2$ is hydrogen; and
  that when R represents hydrogen, X is not OH;
  or the corresponding acid salt of said at least one indole derivative,
  said indole derivative being present in said tinctorial composition in an amount ranging from 0.02 to 5 percent by weight based on the total weight of said tinctorial composition, and optionally one or more components selected from the group consisting of
  a surface-active agent;
  a thickener;
  an indole compound selected from the group consisting of 5,6-dihydroxyindole, 2-methyl-5,6-dihydroxyindole, 6-hydroxyindole and corresponding acid addition salts thereof;
  a direct dye;
  an oxidation dye precursor;
  a coupler; and
  a rapid oxidation dye; rinsing said fibers, drying said fibers after contact thereof with said tinctorial composition, and subsequently applying to said fibers an aqueous alkaline oxidizing solution with a pH between 8.5 and 12, comprising an oxidizing agent present in an amount ranging from 1 to 10 percent by weight based on the total weight of said alkaline oxidizing solution
wherein said oxidizing agent is selected from the group consisting of hydrogen peroxide, urea peroxide, an alkali metal percarbonate, an alkali metal perborate, an ammonium percarbonate and an ammonium perborate.

2. The process of claim 1 wherein said indole derivative of formula (I) is selected from the group consisting of
  7-hydroxy-2,3-dimethyl-4-methoxyindole,
  7-hydroxyindole,
  5-acetoxy-6-hydroxyindole,
  6-hydroxy-2-methyl-5-methoxyindole,
  5,6-di(trimethyl silyloxy)indole and
  2-methyl-4-hydroxy-5-ethoxyindole.

3. The process of claim 1 wherein said indole derivative of formula (I) is present in an amount ranging from 0.05 to 3 percent by weight based on the total weight of said tinctorial composition.

4. The process of claim 1 wherein said cosmetically acceptable medium consists essentially of water or a water-solvent mixture.

5. The process of claim 4 wherein said solvent is selected from the group consisting of ethyl alcohol, propyl alcohol, isopropyl alcohol, tert. butyl alcohol, ethylene glycol, ethylene glycol monomethyl ether, ethylene glycol monoethyl ether, ethylene glycol monobutyl ether, propylene glycol, propylene glycol monomethyl ether, dipropylene glycol monomethyl ether and methyl lactate, said solvent being present in said water-solvent mixture in an amount ranging from 0.5 to 75 percent by weight based on the total weight of said tinctorial composition.

6. The process of claim 5 wherein said solvent is present in said water-solvent mixture in an amount ranging from 2 to 50 percent by weight based on the total weight of said tinctorial composition.

7. The process of claim 5 wherein said solvent is present in said water-solvent mixture in an amount ranging from 2 to 20 percent by weight based on the total weight of said tinctorial composition.

8. The process of claim 1 wherein said tinctorial composition further consist essentially of a surface-active agent and a thickener, each in an amount up to 3 percent by weight based on the total weight of said tinctorial composition.

9. The process of claim 1 wherein said tinctorial composition further consists essentially of a direct dye, an oxidation dye precursor, a coupler or a rapid oxidation dye.

10. The process of claim 1 wherein said aqueous alkaline oxidizing solution contains an alkaline agent selected from the group consisting of ammonia and an alkanolamine.

11. The process of claim 1 wherein said oxidizing agent is present in an amount ranging from 1 to 5 percent by weight based on the total weight of said alkaline oxidizing solution.

12. A two component agent for dyeing keratinous fibers which does not include iodide ions, one component consisting essentially of, in a cosmetically acceptable aqueous medium having a pH less than or equal to 7, one or more indole derivatives of formula (I)

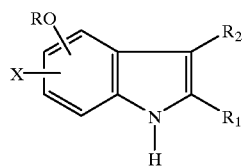

(I)

wherein
R$_1$ represents hydrogen or alkyl,
R$_2$ represents hydrogen or alkyl,
R represents hydrogen, Si(CH$_3$)$_3$ or CO alkyl, and
X represents hydrogen, OH or OSi(CH$_3$)$_3$, or X, when in the 4- or 5-position, also represents O-alkyl on the condition
that when X is in the 5-position and X is as defined above and OR represents OH in the 4- or 6-position, only one of R$_1$ and R$_2$ is other than hydrogen; and
that when X represents hydrogen, OR is in the 7-position and R$_2$ is hydrogen; and
that when R represents hydrogen, X is not OH;
or the corresponding acid salt of said at least one indole derivative,
said indole derivative being present in said tinctorial composition in an amount ranging from 0.02 to 5 percent by weight based on the total weight of said tinctorial composition,
the other component being an aqueous alkaline oxidizing solution with a pH between 8.5 and 12, consisting essentially of an aqueous solution of an oxidizing agent which may be mixed at the time of application with an aqueous alkaline solution, said oxidizing agent being present in an amount ranging from 1 to 10 percent by weight based on the total weight of said alkaline oxidizing solution,
wherein said oxidizing agent is selected from the group consisting of hydrogen peroxide, urea peroxide, an alkali metal percarbonate, an alkali metal perborate, an ammonium percarbonate and ammonium perborate.

13. A two compartment kit for dyeing keratinous fibers wherein said kit does not include iodide ions, one compartment housing a tinctorial composition consisting essentially of, in a cosmetically acceptable aqueous medium having a pH less than or equal to 7 one or more indole derivatives of formula (I)

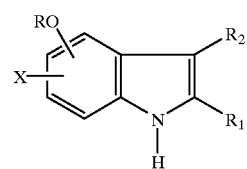

(I)

wherein
R$_1$ represents hydrogen or alkyl,
R$_2$ represents hydrogen or alkyl,
R represents hydrogen, Si(CH$_3$)$_3$ or CO alkyl, and
X represents hydrogen, OH or OSi(CH$_3$)$_3$, or X, when in the 4- or 5-position, also represents O-alkyl on the condition
that when X is in the 5-position and X is as defined above and OR represents OH in the 4- or 6-position, only one of R$_1$ and R$_2$ is other than hydrogen; and
that when X represents hydrogen, OR is in the 7-position and R$_2$ is hydrogen; and
that when R represents hydrogen, X is not OH;
or the corresponding acid salt of said at least one indole derivative,
said indole derivative being present in said tinctorial composition in an amount ranging from 0.02 to 5 percent by weight based on the total weight of said tinctorial composition,
and a second compartment housing an aqueous alkaline oxidizing solution with a pH between 8.5 and 12 consisting essentially of an aqueous alkaline solution and an aqueous solution of an oxidizing agent which are mixed at the time of application, said oxidizing agent being present after mixing in an amount ranging from 1 to 10 percent by weight based on the total weight of said alkaline oxidizing solution,
wherein said oxidizing agent is selected from the group consisting of hydrogen peroxide, urea peroxide, an alkali metal percarbonate, an alkali metal perborate, an ammonium percarbonate, and ammonium perborate.

14. A process for dyeing keratinous fibers, which does not include iodide ions, consisting essentially of initially applying to said fibers a tinctorial composition consisting essentially of, in a cosmetically acceptable medium having a pH less than or equal to 7, an indole derivative selected from the group consisting of 7-hydroxy-2,3-dimethyl-4-methoxyindole, 7-hydroxyindole, 5-acetoxy-6-hydroxyindole, 6-hydroxy-2-methyl-5-methoxyindole, 5,6-di(trimethyl silyloxy) indole and 2-methyl-4-hydroxy-5-ethoxyindole, said indole derivative being present in said tinctorial composition in an amount ranging from 0.02 to 5 percent by weight based on the total weight of said tinctorial composition, rinsing said fibers, drying said fibers after contact thereof with said tinctorial composition and subsequently applying to said fibers an aqueous alkaline oxidizing solution comprising an oxidizing agent present in an amount ranging from 1 to 10 percent by weight based on the total weight of said alkaline oxidizing solution, wherein said oxidizing agent is selected from the group consisting of hydrogen peroxide, urea peroxide, an alkali metal percarbonate, an alkali metal perborate, an ammonium percarbonate, and ammonium perborate.

15. In a process for dyeing keratinous fibers consisting essentially of applying to said fibers a tinctorial composition containing, in a cosmetically acceptable medium having a pH less than or equal to 7, an indole derivative, rinsing said fibers, drying said fibers after contact thereof with said tinctorial composition and subsequently applying to said fibers an aqueous alkaline oxidizing solution with a pH between 8.5 and 12, the improvement wherein said tinctorial composition contains at least one indole derivative of formula (I)

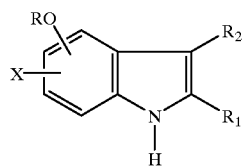

(I)

wherein
$R_1$ represents hydrogen or alkyl,
$R_2$ represents hydrogen or alkyl,
R represents hydrogen, $Si(CH_3)_3$ or CO alkyl, and
X represents hydrogen, OH or $OSi(CH_3)_3$, or X, when in the 4- or 5-position, also represents O-alkyl on the condition
that when X is in the 5-position and X is as defined above and OR represents OH in the 4- or 6-position, only one of $R_1$ and $R_2$ is other than hydrogen; and
that when X represents hydrogen, OR is in the 7-position and $R_2$ is hydrogen; and
that when R represents hydrogen, X is not OH;
and the corresponding acid salt of said at least one indole derivative,
said indole derivative being present in said tinctorial composition in an amount ranging from 0.02 to 5 percent by weight based on the total weight of said tinctorial composition,
said process not including iodide ions,
and wherein said oxidizing agent is selected from the group consisting of hydrogen peroxide, urea peroxide, an alkali metal percarbonate, an alkali metal perborate, an ammonium percarbonate, and ammonium perborate.

16. A process for dyeing keratinous fibers, without iodide ions, consisting essentially of initially applying to said fibers a tinctorial composition consisting essentially of, in a cosmetically acceptable medium having a pH less than or equal to 7, one or more indole derivatives of formula (I)

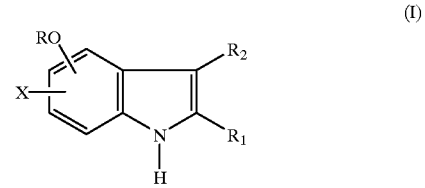

(I)

wherein
$R_1$ represents hydrogen or alkyl,
$R_2$ represents hydrogen or alkyl,
R represents hydrogen, $Si(CH_3)_3$ or CO alkyl, and
X represents hydrogen, OH or $OSi(CH_3)_3$, or X, when in the 4- or 5-position, also represents O-alkyl on the condition
that when X is in the 5-position and X is as defined above and OR represents OH in the 4- or 6-position, only one of $R_1$ and $R_2$ is other than hydrogen; and
that when X represents hydrogen, OR is in the 7-position and $R_2$ is hydrogen; that when R represents hydrogen, X is not OH;
or the corresponding acid salt of said at least one indole derivative,
said indole derivative being present in said tinctorial composition in an amount ranging from 0.02 to 5 percent by weight based on the total weight of said tinctorial composition, and optionally one or more components selected from the group consisting of
a surface-active agent;
a thickener;
an indole compound selected from the group consisting of 5,6-dihydroxyindole, 2-methyl-5,6-dihydrxyindole, 6-hydroxyindole and corresponding acid addition salts thereof;
a direct dye;
an oxidation dye precursor;
a coupler; and
a rapid oxidation dye; rinsing said fibers, drying said fibers after contact thereof with said tinctorial composition, and subsequently applying to said fibers an aqueous alkaline oxidizing solution with a pH between 8.5 and 12, comprising an oxidizing agent present in an amount ranging from 1 to 10 percent by weight based on the total weight of said alkaline oxidizing solution
wherein said oxidizing agent is selected from the group consisting of hydrogen peroxide, urea peroxide, an alkali metal percarboniate, an alkali metal perborate, an ammonium percarbonate and an ammonium perborate;
and additionally said tinctorial composition also further consists essentially of another indole compound other than said indole derivative of formula (I), said another indole compound being selected from the group consisting of 5,6-dihydroxyindole, 2-methyl-5,6-dihydroxyindole, 6-hydroxyindole and corresponding acid addition salts thereof.

* * * * *